United States Patent [19]

Muehlenbein et al.

[11] Patent Number: 5,621,220

[45] Date of Patent: Apr. 15, 1997

[54] APPARATUS FOR EVALUATING MEASURING VALUES

[75] Inventors: Rudolf Muehlenbein, Grafschaft; Karlheinz Schaust, Fachbach; Holger Tuitje, Neuwied, all of Germany

[73] Assignee: Honeywell AG, Offenbach, Germany

[21] Appl. No.: 420,953

[22] Filed: Apr. 12, 1995

[30] Foreign Application Priority Data

Apr. 14, 1994 [EP] European Pat. Off. ............... 94105756

[51] Int. Cl.⁶ .................................................. G01N 21/84
[52] U.S. Cl. ................. 250/559.48; 250/339.02; 250/341.7; 356/430
[58] Field of Search ........................... 250/339.09, 252.1, 250/339.11, 339.12, 359.1, 339.02, 341.7, 559.03, 559.04, 559.06, 559.4, 559.46, 559.48, 208.2; 356/51, 73, 430, 429, 431, 440

[56] References Cited

U.S. PATENT DOCUMENTS

| | | | |
|---|---|---|---|
| 3,859,538 | 1/1975 | Mannonen | 250/341.7 |
| 3,898,469 | 8/1975 | Nichols et al. | 250/559.06 |
| 4,773,029 | 9/1988 | Claesson et al. | 250/359.1 |
| 4,879,471 | 11/1989 | Dahlquist | 250/559.06 |
| 5,256,883 | 10/1993 | Weichmann et al. | 356/430 |

Primary Examiner—Hezron E. Williams
Assistant Examiner—Richard A. Moller
Attorney, Agent, or Firm—Arthur A. Sapelli

[57] ABSTRACT

An apparatus evaluates measuring values from a laminar material, wherein the laminar material is moving in a single plane in a predetermined direction, the laminar material being moved also being under test. The apparatus comprises a measuring platform which is being moved traverse to a direction of movement of the laminar material. Further, the measuring platform is tiltable about an axis which is normal to a plane of the laminar material, an angle of tilt ($á$) being determined by a traversing velocity ($v_t$) of the measuring platform and velocity ($v_b$) of the predetermined direction of the laminar material. A plurality of separated sensors and radiation emitters are mounted on the measuring platform, and in conjunction with the angle of tilt cause, the measuring valves acquired from the different sensors to be from the same measuring spot of the laminar material.

6 Claims, 6 Drawing Sheets

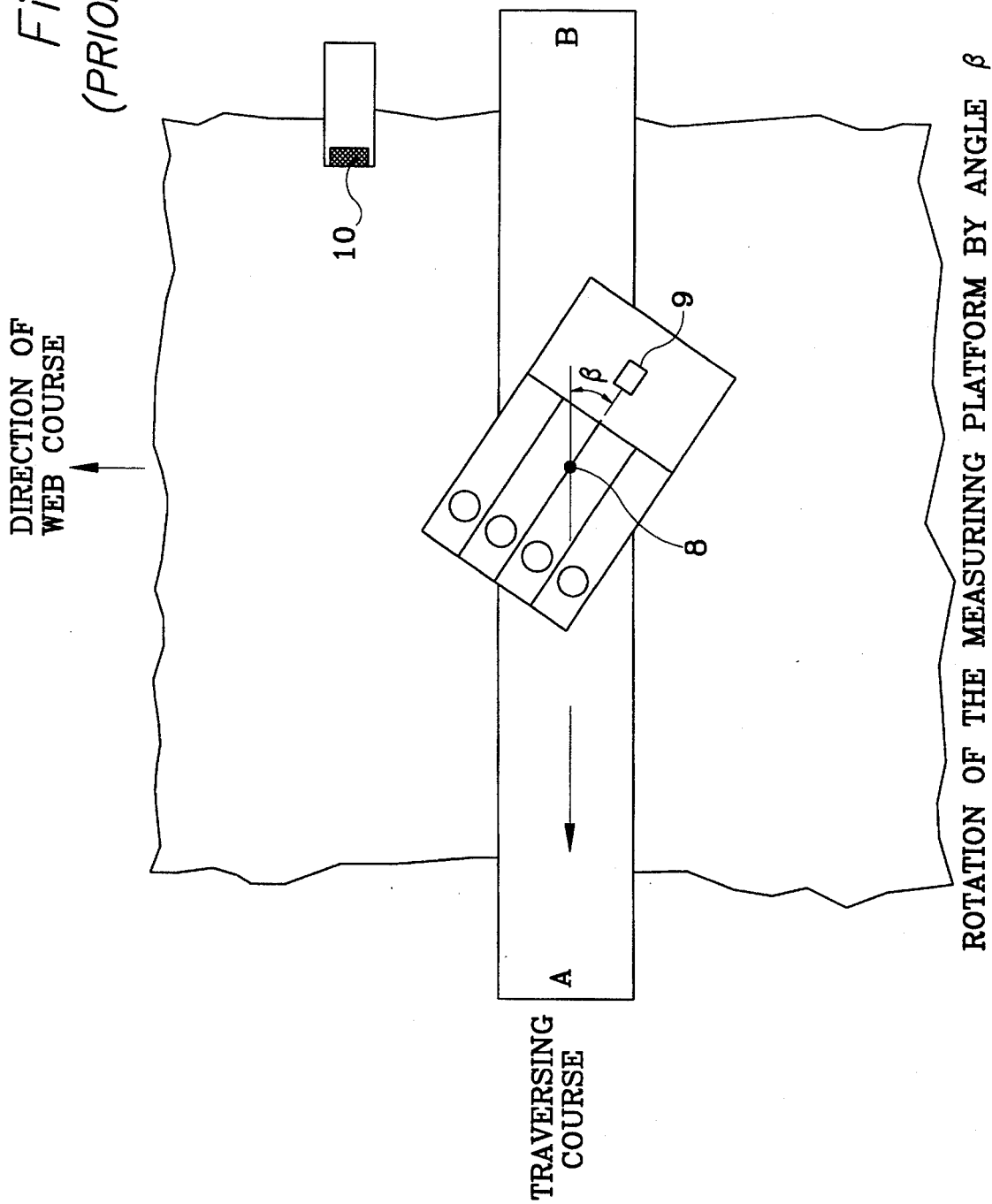

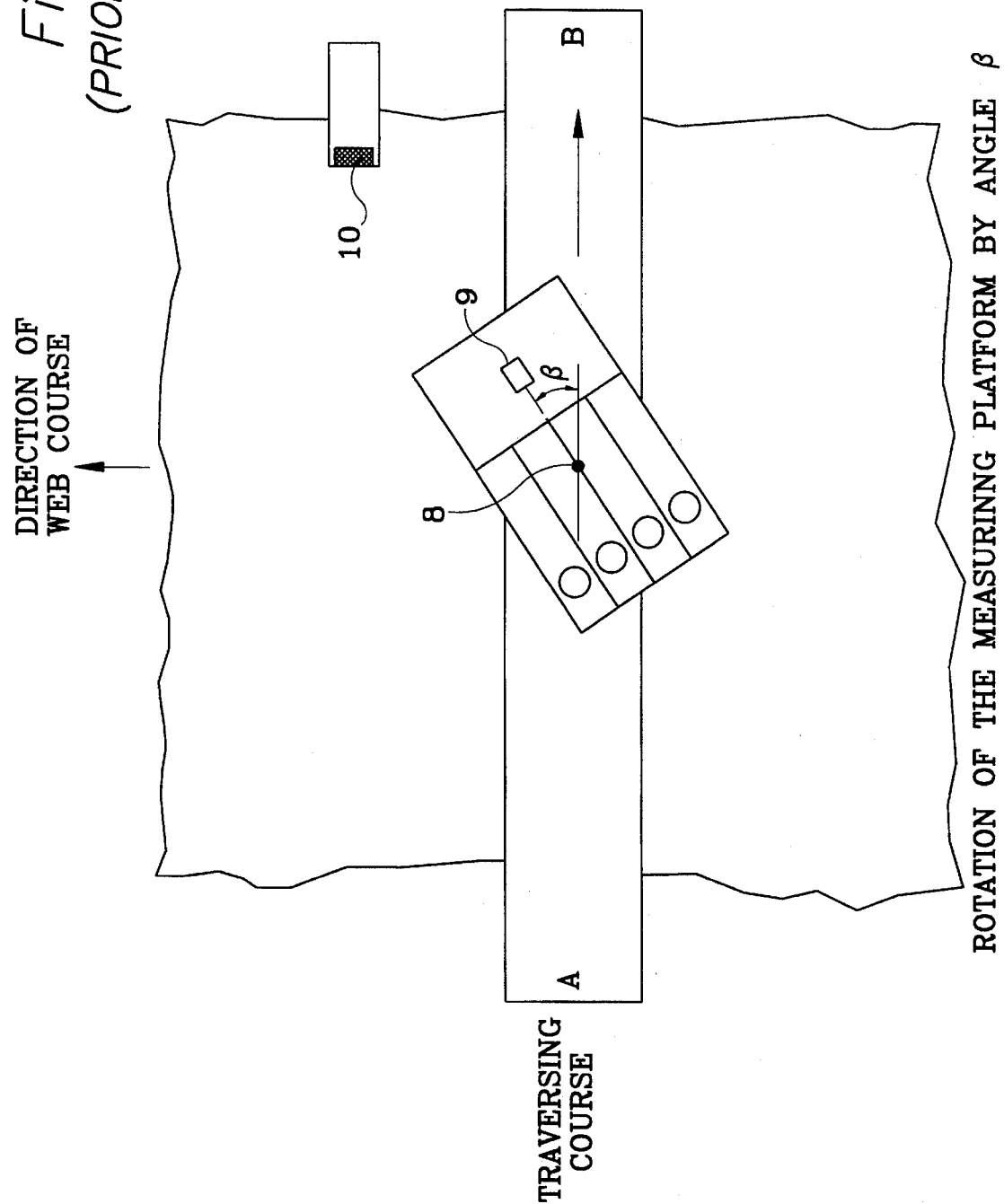

APPARATUS FOR EVALUATING MEASURING VALUES

BACKGROUND OF THE INVENTION

The present invention relates to an apparatus for evaluating measuring values, and more particularly, to an apparatus for evaluating measuring values from moving laminar materials under test.

For the quality control and the on-line process control of laminar materials under test as for instance paper, plastic foils, webs of fabric or sheets of metal, certain characteristics of such materials under test are sensed, whereas it is known to explore the material under test with a traversing measuring device. For the exploration of paper webs, e.g., the material under test can be irradiated with infra-red (IR) radiation of different wave lengths, and by means of evaluating the reflected or transmitted radiation intensities and by an accompanying computation the desired measured values can be evaluated. The different IR rays of different wave lengths may be produced from a single radiation source by a filter wheel and may be sensed by a detector. However, the rays of such a source could also be separated into different channels by a chopper device and a beam splitter and a filter element, and could be applied to different detectors. Examples of this can be taken from U.S. Pat. Nos. 4,300,049 and 3,405,268.

With a measuring device traversing the material under test and with the material under test being moved, a problem exists that the rays of different wavelength impinge on the material under test on different spots, such that system errors produced thereby do not allow an optimum control of the process. With respect to a high speed evaluation of the measuring data for a quick control of the quality features of the material under test, the traversing velocity of the measuring platform can be increased which results in an increase distance between the different measuring points of the sensors, and therefore results in a greater measuring error.

Thus, there is a need to provide a device for evaluating measuring values in which the measuring values can be acquired from the same measuring spot of the material under test.

SUMMARY OF THE INVENTION

Thus, there is provided by the present invention, a device for evaluating measuring values which are acquired from the same measuring spot of the material under test. The apparatus of the present invention evaluates measuring values from a laminar material, wherein the laminar material is moving in a single plane in a predetermined direction, the laminar material being moved also being under test. The apparatus comprises a measuring platform which is being moved traverse to a direction of movement of the laminar material. Further, the measuring platform is tiltable about an axis which is normal to a plane of the laminar material, an angle of tilt (β) being determined by a traversing velocity ($v_t$) of the measuring platform and a velocity ($v_b$) of the predetermined direction of the laminar material. A plurality of separated sensors and radiation emitters are mounted on the measuring platform, and in conjunction with the angle of tilt cause the measuring valves acquired from the different sensors to be from the same measuring spot of the laminar material.

Accordingly, it is an object of the present invention to provide an apparatus for evaluating measuring values whereby the measuring values are acquired for the same measuring spot of the material under test.

It is another object of the present invention to provide an apparatus for evaluating measuring values from moving laminar materials under test whereby the measuring values are acquired from the same measuring spot of the material under test.

It is still another object of the present invention to provide an apparatus for evaluating measuring values from moving laminar materials under test by a measuring platform moved across the moving material under test whereby the measuring values are acquired from the same measuring spot of the material under test.

These and other objects of the present invention will become more apparent when taken in conjunction with the following description and attached drawings, wherein like characters indicate like parts, and which drawings form a part of the present application.

BRIEF DESCRIPTION OF THE DRAWINGS

FIG. 4a shows the exploration of the material under test by a measuring device of the present invention when in a first traversing direction;

FIG. 4b shows the exploration of the material under test by a measuring device of the present invention when traversing in a second direction.

DETAILED DESCRIPTION

Figure 1:
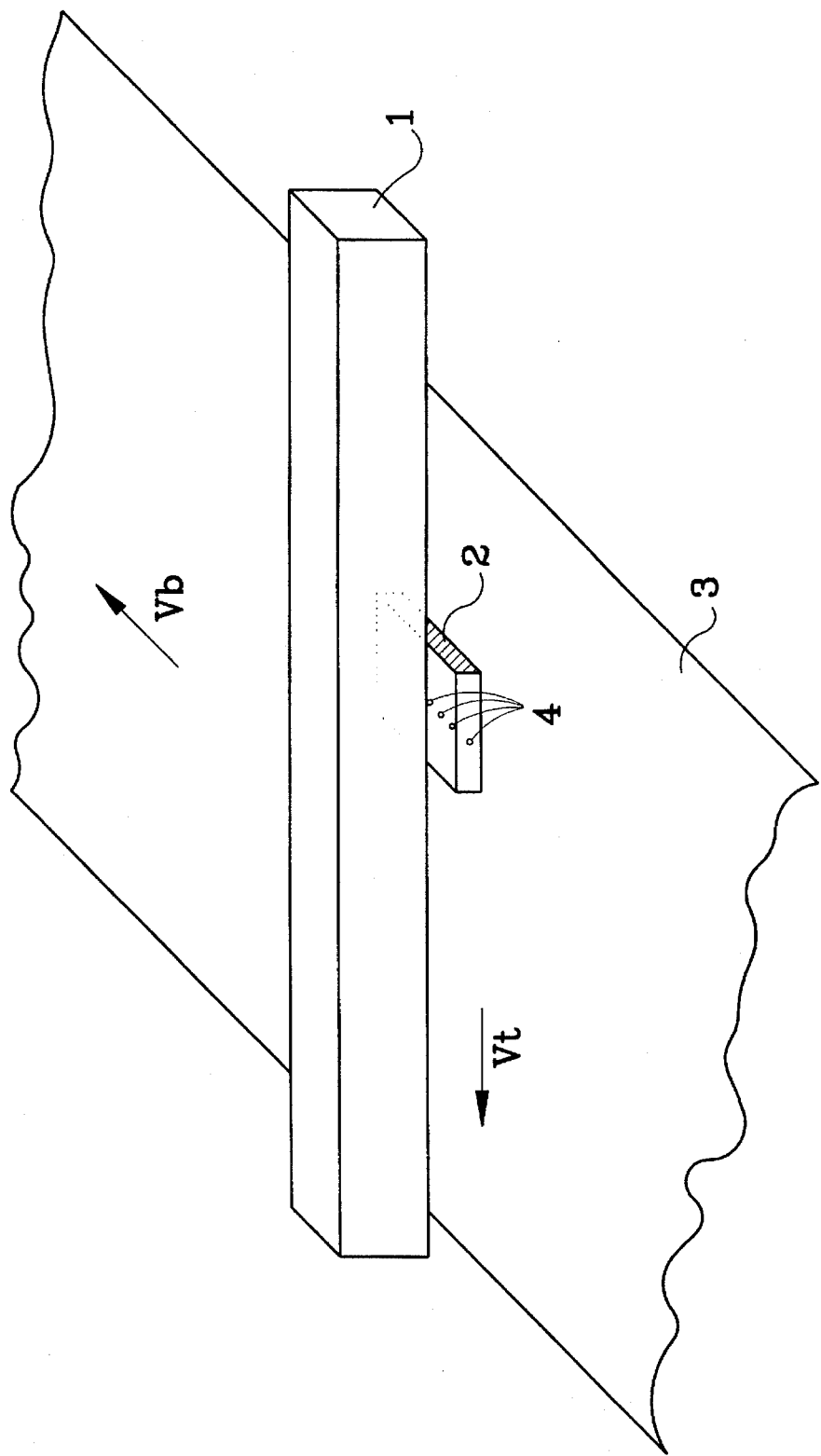
FIG. 1 shows the basic measuring device according to the prior art with the measuring platform on a crossbeam over the material under test.

Referring to FIG. 1, there is shown an apparatus for evaluating measuring values of the prior art, whereby a measuring platform 2 is guided by a crossbeam 1 over a material under test 3 which is moved with the velocity $v_b$. The measuring platform 2 has a plurality of sensors or detectors 4, respectively, which are arranged at equal distances.

Figure 2:
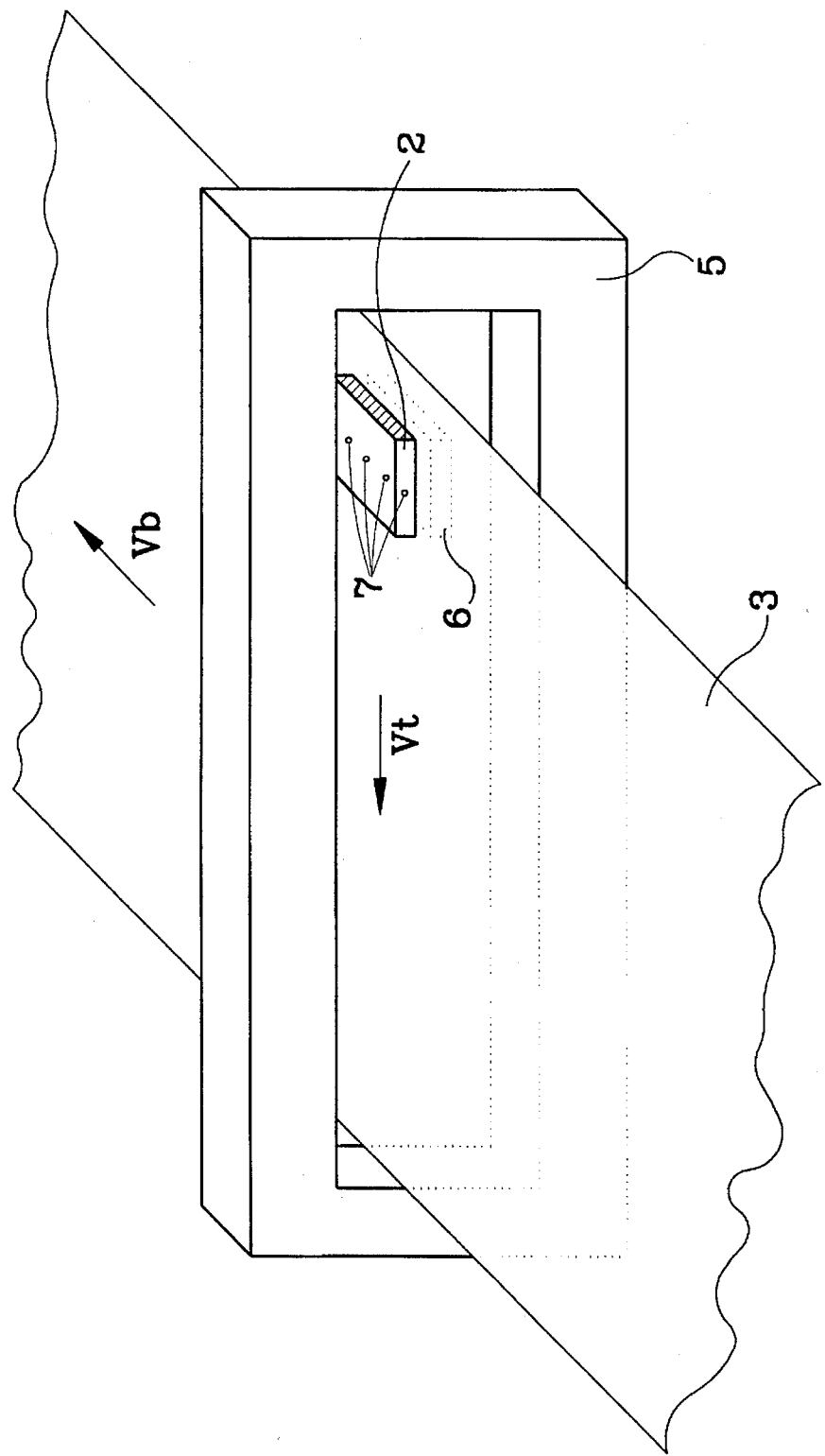
FIG. 2 shows another measuring device according to the prior art with a two-piece measuring platform guided by an O-shaped support over the material under test.

Referring to FIG. 2, there is shown another apparatus for evaluating measuring values of the material under test 3 according to the prior art. The measuring platform additionally comprises a lower part 6, whereas the upper part 2 and the lower part 6 have the material under test in-between them. The sensors 4 are arranged on a straight measuring line 7. Both parts 2, 6 of the measuring platform are guided on an O-shaped crossbeam 5.

It is well known to one skilled in the art, that such measurements can be done with the reflected light as well as with the transmitted light. In a first case, e.g., a radiation source within the measuring platform 2, irradiates the material under test 3, and the sensors or detectors 4 (radiation receivers), respectively, receive the reflected radiation by filters arranged in front of them. In a second case, e.g., the radiation source is arranged in the lower part 6 of the measuring platform, the radiation is received in the transmitted light by the sensors 4 arranged on the measuring line 7. As an alternative, instead of a single radiation source, a plurality of radiation sources of different wavelengths can be used.

Figure 3:
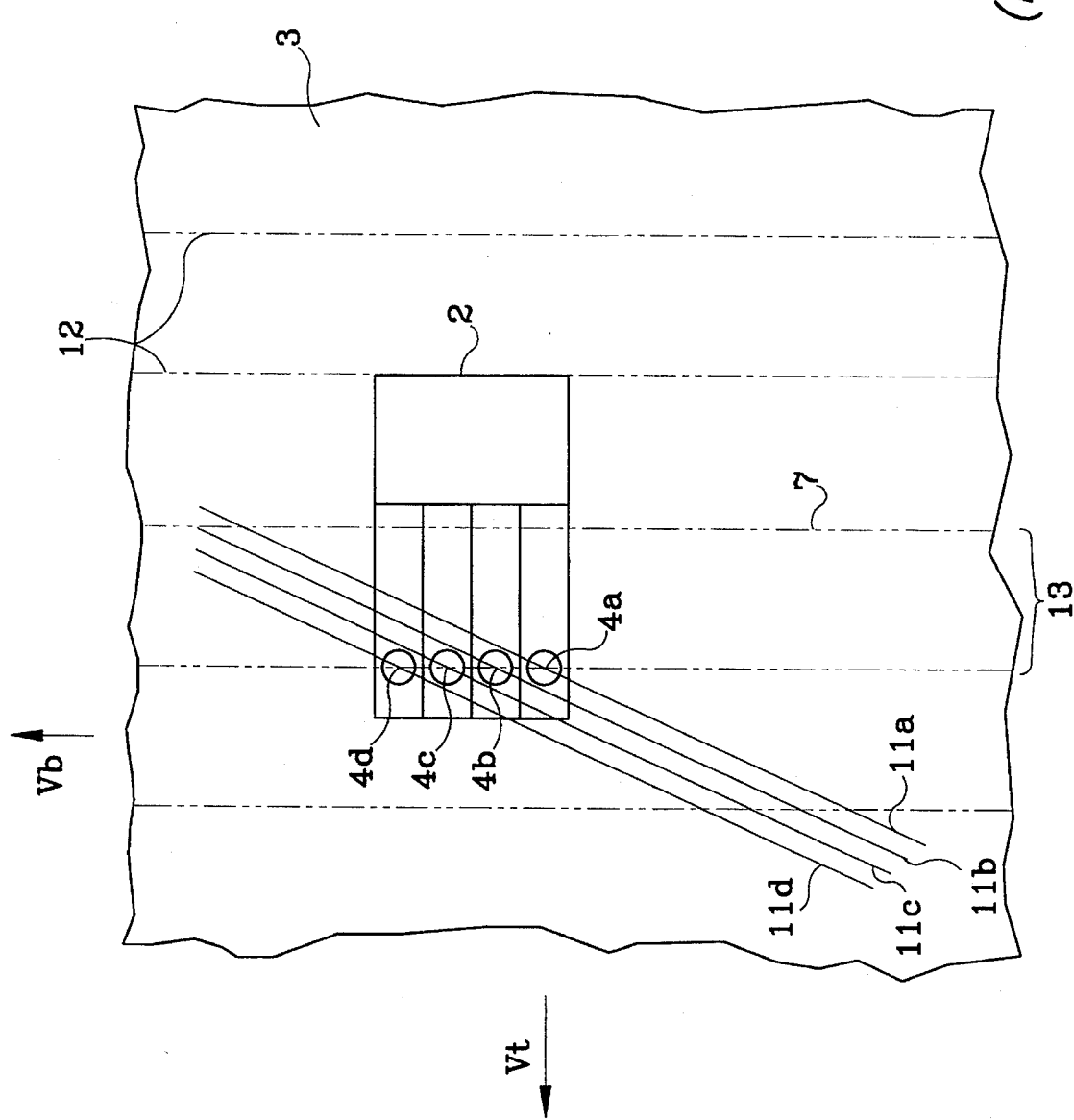
FIG. 3 shows the exploration of the material under test by the measuring device according to the prior art.

With such a known device for evaluating measuring values is not possible to acquire measured values from the same measuring spot of the material under test i.e., to implement a so-called "same-spot" measurement as can be taken from FIG. 3. Referring to FIG. 3, there is shown an apparatus for evaluating measuring values of the prior art such that Within a traverse profile element 13, a sensor 4a is exploring a measuring lane 11a, a sensor 4b is exploring a measuring lane 11b, . . .

Figure 5:
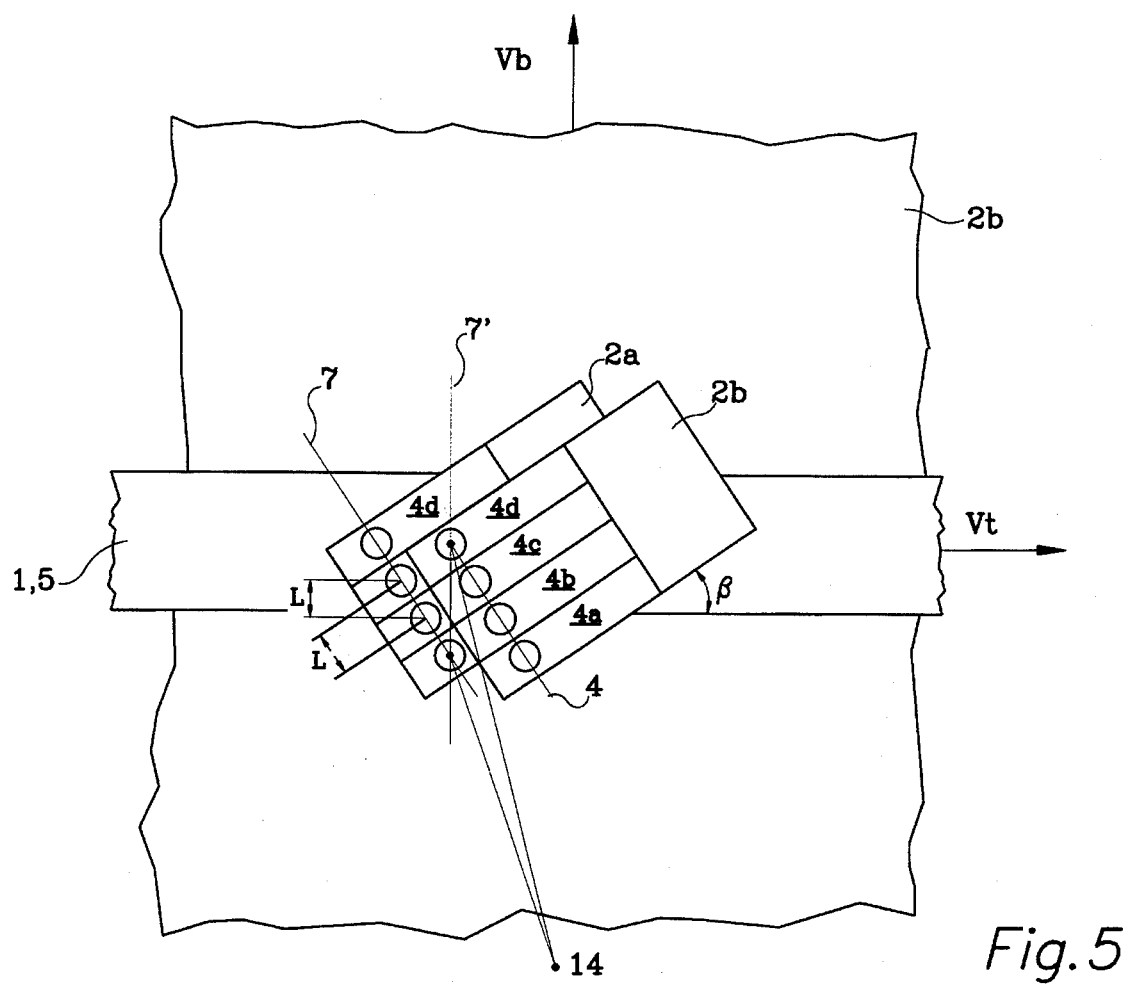
FIG. 5 shows an illustration of the measuring platform in two different positions for purposes of explaining the present invention.

The present invention provides a solution to the aforementioned problem and will now be described hereinunder with reference to FIGS. 4a, 4b, and 5. FIGS. 4a and 4b show the exploration of the material under test when traversing in a first and second direction, respectively. FIG. 5 shows an illustration of the measuring platform in two different positions. For a simple explanation it is assumed that e.g., four sensors 4a to 4d spaced apart under equal distances L are arranged on a measuring line 7. For instance each sensor consists of an infrared radiation detector having an interference filter in front of it and being illuminated by the reflected or transmitted light of an infrared radiation source.

According to the invention, the measuring platform 2 and 6 are rotated by an angle β about an axis 8 which is normal to the crossbeam 1, 5, and to the material under test 3, the angle β is evaluated as follows:

$$\tan \beta = v_t/v_b,$$

where $v_t$ is the traversing velocity of the measuring platform and $v_b$ is the velocity of the web. Both values $v_t$ and $v_b$ are evaluated by respective measuring devices 9 and 10.

At a reversal of the traversing direction of the measuring platform, the sign for the angle β changes respectively. Accordingly, there is provided, but not shown, driving devices each driving the angle adjustment of the measuring platform at the reversal point according to the actual velocity of the web and the traversing platform.

Referring to FIG. 5, there is shown the measuring platform tilted by the angle β, at two different points of time. At the position 2a the sensor 4a is exploring the measuring spot 14. At the position 2b the sensor 4d is exploring the measuring spot 14. The exploration by two adjacent sensors is delayed by the time $$\Delta t = L'/v_b,$$

where L' corresponds to the distance of the sensors in the direction of movement of the material under test on the measuring line 7'. The distance L' may be calculated from the distance L of the different adjacent sensors in the direction of the measuring line 7 according to the following relationship:

$$L' = L' \cos \beta$$

Therefore, the sensor 4d, at a point of time $t_2 = 4 \cdot \Delta t$ in the position 2b of the measuring platform is exploring the same measuring spot 14 as the sensor 4a at the position 2a of the measuring platform which corresponds to a "same-spot" measurement.

Thus, for instance, the atro basis weight can only be calculated by the accounting of the known humidity contents with the lutro basis weight burdened with humidity. The measuring of the basis weight mostly is done with a radiometric sensor. However, measuring of humidity is done with an infrared radiation sensor. The atro basis weight of the material under test only can be done with a mathematic calculation within a measuring model so that the real atro basis weight only can be acquired by a "same-spot" measurement.

While there has been shown what is considered the preferred embodiment of the present invention, it will be manifest that many changes and modifications can be made therein without departing from the essential spirit and scope of the invention. It is intended, therefore, in annexed claims to cover all such changes and modifications which fall within the true scope of the invention.

We claim:

1. An apparatus for evaluating measuring values from a laminar material, wherein the laminar material is moving in a single plane in a predetermined direction, comprising:

a) a measuring platform, which is being moved in the direction traverse to a direction of movement of the laminar material, and further wherein the measuring platform is rotatable about an axis which is normal to a plane of the laminar material, an angle of rotation (β) being determined by a traversing velocity ($v_t$) of the measuring platform and a velocity ($v_b$) of the predetermined direction of the laminar material; and b) a plurality of separated sensors and radiation emitters mounted on said measuring platform, the sensors and radiation emitters being mounted such that, in conjunction with the angle of rotation, the measuring values acquired from the plurality of sensors is from a same measuring spot of the laminar material.

2. An apparatus according to claim 1 wherein the angle of rotation has a different sign as a function of the direction of the traverse movement of the measuring platform.

3. An apparatus according to claim 1 wherein the sensors and radiation emitters are equally spaced a distance (L) on a measuring line.

4. An apparatus according to claim 3, wherein the acquisition of the measuring values by the sensors and excitation of the radiation emitters is done with a time delay, the time delay Δt between scanning of two adjacent sensors and between the excitation of two adjacent radiation emitters is in accordance with a relationship defined by:

$$\Delta t = L'/v_b$$

where L' is evaluated by $$L' = L \cos \beta.$$

5. An apparatus according to claim 4, wherein the angle of rotation is given by:

$$\tan \beta = v_t/v_b.$$

6. An apparatus according to claim 5, further comprising: a first and a second measuring device, said first measuring device for determining the traversing velocity ($v_t$) of the measuring platform, and said second measuring device for determining the velocity ($v_b$) of the laminar material.

* * * * *